United States Patent [19]

Kao et al.

[11] 4,170,709

[45] Oct. 9, 1979

[54] 16-KETO PGE$_2$ METHYL ESTERS

[75] Inventors: Wenling Kao, King of Prussia; Richard W. Rees, Bryn Mawr, both of Pa.

[73] Assignee: American Home Products Corporation, New York, N.Y.

[21] Appl. No.: 838,614

[22] Filed: Oct. 3, 1977

[51] Int. Cl.$^2$ ............................................. C07C 177/00
[52] U.S. Cl. ..................................... 560/121; 424/305; 424/317; 562/503; 542/429
[58] Field of Search .................. 560/121; 260/514 D; 562/503

[56] References Cited

U.S. PATENT DOCUMENTS

| 3,932,463 | 1/1976 | Schaub et al. ................... 260/340.7 |
| 4,004,020 | 1/1977 | Skuballa et al. ..................... 424/278 |

FOREIGN PATENT DOCUMENTS

| 2605584 | 8/1976 | Fed. Rep. of Germany ........... 560/121 |
| 50148334 | 11/1975 | Japan ....................................... 560/121 |

*Primary Examiner*—Robert Gerstl

[57] ABSTRACT

The preparation of the methyl esters of 16-keto prostaglandin E$_2$ and 15-epi-16-keto prostaglandin E$_2$ is described. The compounds have hypotensive activity.

3 Claims, 2 Drawing Figures

FIGURE I
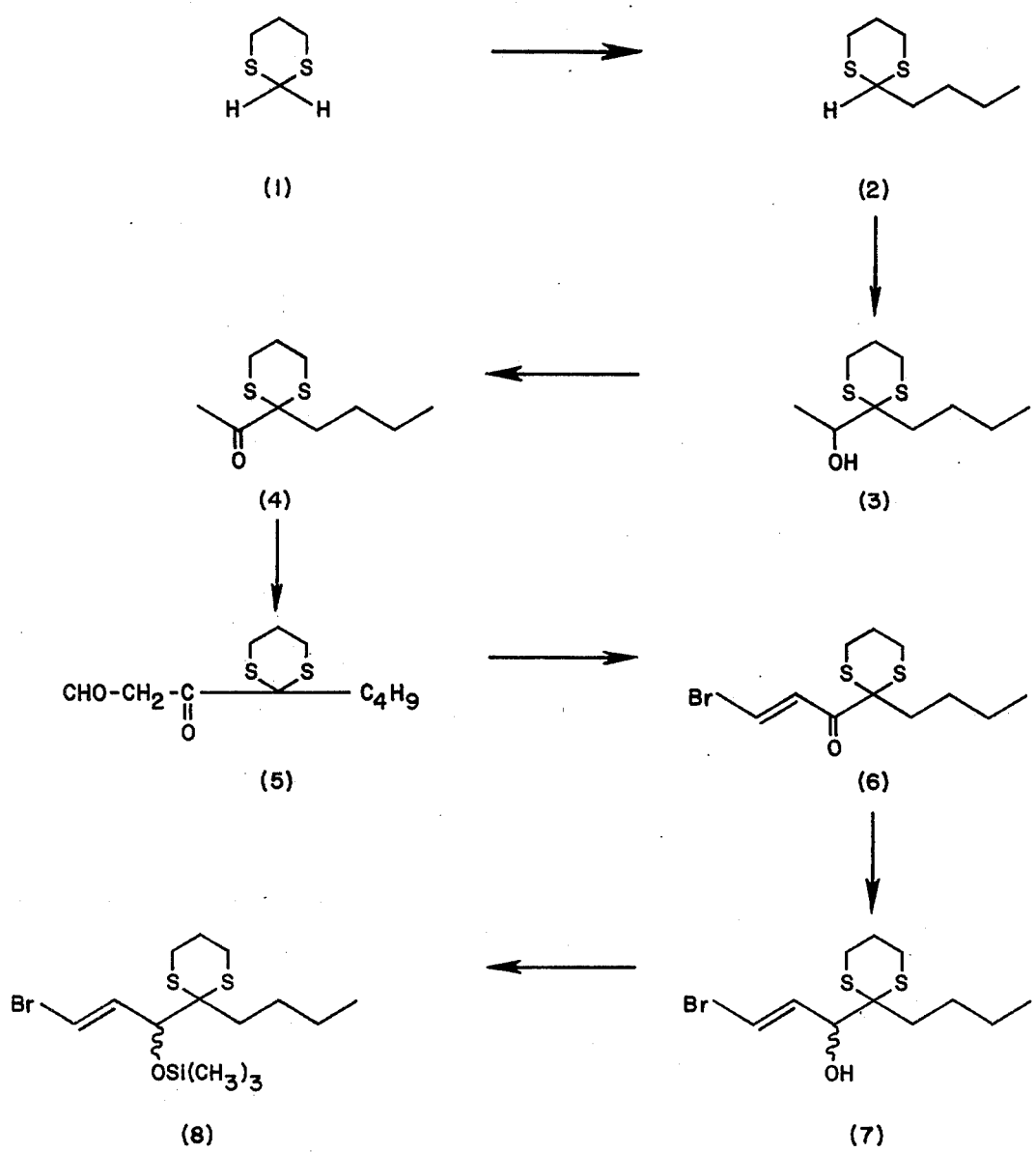

FIGURE II
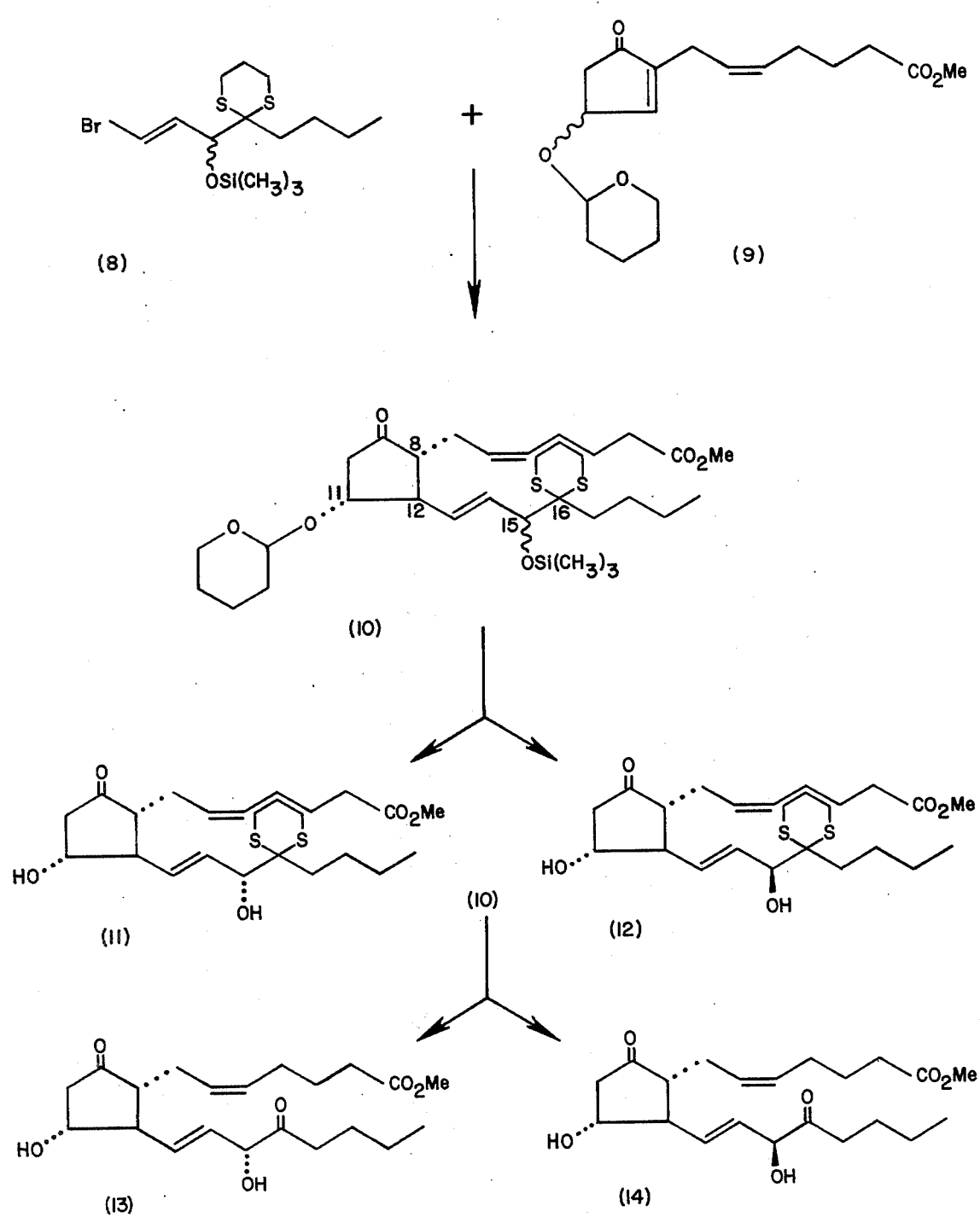

16-KETO PGE₂ METHYL ESTERS

This invention relates to 16-keto prostaglandin $E_2$ and to the non-toxic, pharmaceutically acceptable salts and esters thereof.

Various 16-substituted prostaglandins are known in the literature. Among these compounds are 16,16-dimethyl prostaglandin $E_2$ [B. Magerlein et al., *Prostaglandins*, 4, 143 (1973)]; 16-methylene prostaglandin $E_2$ [H. Miyake et al., *Chemistry Letters*, 211 (1976)]; 16-ethano prostaglandin $E_2$ [Miyake et al., supra]; and 16-methyl prostaglandin $E_2$ [M. Hayashi et al., *J. Org. Chem.*, 38, 1250 (1973)]. 16-Thioketal prostaglandin $E_2$ methyl ester and 16-keto dihydro prostaglandin $E_1$ methyl ester are described in German Offenlegungsschrift No. 26 05 584 (October, 1976) and in Belgian Pat. No. 838,582 (Aug. 13, 1976).

The invention sought to be patented comprises a compound of the formula:

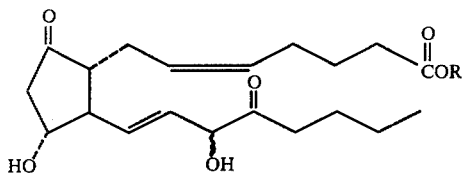

wherein R is hydrogen, an alkyl group of from 1 to 6 carbon atoms, an alkali metal, or a pharmaceutically acceptable, non-toxic cation derived from ammonia or a basic amine.

It will be apparent to those skilled in the art that the carbon atom to which is attached the hydroxyl group at the C-15 position is an assymetric carbon, and, as a consequence the hydroxyl group at this position can be in either of two epimeric configurations. The wavy line (∿) at the C-15 position of the formulae depicted herein and in the claims indicates that the hydroxyl group can be in the α-(natural) or β-(epi) configuration. Hence, this invention contemplates the compounds of Formula I in either the 15-α or 15-β form, or in mixtures thereof.

The compounds of Formula I possess hypotensive activity as evidenced by pharmacological evaluation in rats according to standard test procedures. For example, the compounds of Formula I wherein R is methyl when administered I.V. to normotensive rats, lowered blood pressure either as much as prostaglandin $E_2$ (for the 15-α isomer) or 10% as much as prostaglandin $E_2$ (for the 15-β isomer).

The general method of synthesis of the compounds of Formula I, wherein R is an alkyl group, is illustrated schematically in FIGS. I and II of the annexed Drawing which depicts the preparation of 16-keto prostaglandin $E_2$ methyl ester and 16-keto-15-epi prostaglandin $E_2$ methyl ester. Referring now to FIGS. I and II, wherein the compound formulae are assigned numbers in parentheses for identification, 1,3-dithiane (1) is treated with n-butyl lithium to form the lithio derivative which is reacted with 1-bromo-n-butane to give n-butyldithiane (2). A second lithiation of n-butyldithiane followed by treatment with acetaldehyde provides 3,3-trimethylenedithio-heptan-2-ol (3). This alcohol is oxidized with modified Collins reagent to the methyl ketone (4) which is acylated with ethylformate to give the β-ketoaldehyde (5). Reaction of the β-ketoaldehyde (5) [in the hydroxymethylene form] with triphenylphosphine dibromide affords the trans-1-bromo-enone (6).

The enone (6) is reduced with sodium borohydride to the allylic alcohol (7) which is silylated with trimethylchlorosiline and imidazol to give the derivative (8) wherein the hydroxyl group is protected by the silyl group. The protected derivative is then reacted with cyclopentanone (9) in order to form the C-12 side chain of the prostaglandin. This is accomplished by the conjugate addition of the derivative (8) to the cyclopentanone (9) via the lithium-copper complex, according to the method of H. O. House, *J. Org. Chem.*, 34, 3615 (1969), using the specific conditions developed by E. J. Corey, *J. Am. Chem. Soc.*, 94, 7210 (1972). By analogy to previous findings reported in the literature, the cyclopentane ring of the addition product (10) is assumed to be in the trans-configuration. The addition product (10) is obtained as a mixture of two C-15 epimeric racemates. Removal of the hydroxyl protecting group with aqueous acetic acid gives (+)-16-thioketal prostaglandin $E_2$ methyl ester (11) and its C-15 epimer (12) which were separated by thin layer chromatography. Although it is not possible to determine the configuration at C-15 by spectroscopic analyses (because the spectra are similar), the configuration at C-15 is established by chromatographic mobilities by analogy with the chromatographic behavior previously established for various prostaglandins isomeric at the C-15 position. The less mobile (more polar) product is assigned the 15-α (natural) configuration (11); while the more mobile (less polar) product is assigned the 15-β (epi) configuration (12). The (+)-16-keto prostaglandin $E_2$ methyl esters (13) and (14) were obtained from the epimeric mixture (10) by treatment with silver nitrate/N-chlorosuccinimide to remove the thio ketal group followed by acid hydrolysis (aqueous acetic acid) to remove the tetrahydropyran group. The resulting C-15 epimers were separated into the 15-α (natural) compound (13), and the 15-β (epi) compound (14), by column chromatography. Again the configuration at C-15 is assigned by chromatographic behavior, the 15β-alcohol (14) being less polar than the 15α-alcohol (13).

While the reaction sequence above-described and depicted in FIGS. I and II produces the embodiments of Formula I wherein R is methyl, it will be apparent to those skilled in the art that the various embodiments wherein R is an alkyl group other than methyl can be prepared by substituting an appropriate alkyl ester in place of the methyl ester (9) in the reaction step involving the addition of the side chain moiety to the cyclopentanone ring. When it is desired to prepare an embodiment of Formula I when R is hydrogen (i.e., the free carboxylic acid) a compound of Formula I wherein R is alkyl can be hydrolyzed in known manner.

The alkali metal carboxylates of the invention can be prepared by mixing stoichiometrically equivalent amounts of the free acids of Formula I, preferably in aqueous solution, with solutions of alkali metal bases, such as sodium, potassium, and lithium hydroxides or carbonates, and the like, then freeze drying the mixture to leave the product as a residue. The amine salts can be prepared by mixing the free acids, preferably in solution, with a solution of the appropriate amine in water, isopropanol, or the like, and freeze drying the mixture to leave the product as a residue.

The term "alkyl of from 1 to about 6 carbon atoms" when used herein and in the appended claims includes straight and branched hydrocarbon radicals, illustrative members of which are methyl, ethyl, n-propyl, i-propyl, n-butyl, t-butyl, n-pentyl, n-hexyl, 3-methylpentyl, 2-3-dimethylbutyl, and the like. "Alkali metal" includes, sodium, potassium or lithium. A "pharmaceutically acceptable non-toxic cation derived from ammonia or a basic amine" contemplates the positively charged ammonium ion and analogous ions derived from organic nitrogenous bases strong enough to form such cations. Bases useful for the purpose of forming pharmacologically-acceptable non-toxic addition salts of such compounds containing free carboxyl groups form a class whose limits are readily understood by those skilled in the art. Merely for illustration, they can be said to comprise, in cationic form, those of the formula:

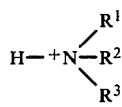

wherein $R^1$, $R^2$, and $R^3$, independently, are hydrogen, alkyl of from about 1 to about 6 carbon atoms, cycloalkyl of from about 3 to about 6 carbon atoms, monocarbocyclicaryl of about 6 carbon atoms, monocarbocyclicarylhydroxyalkyl of from about 7 to about 15 carbon atoms or when taken together with the nitrogen atom to which they are attached, any two of $R^1$, $R^2$, and $R^3$ from part of a 5 to 6-membered heterocyclic ring containing carbon, hydrogen, oxygen, or nitrogen, said heterocyclic rings and said monocarbocyclicaryl groups being unsubstituted or mono- or dialkyl substituted, said alkyl groups containing from about 1 to about 6 carbon atoms. Illustrative therefore of R groups comprising pharmacologically-acceptable cations derived from ammonia or a basic amine are ammonium, mono-, di-, and trimethylammonium, mono-, di-, and triethylammonium, mono-, di-, and tripropylammonium (iso and normal) ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butylpiperidinium, 2-methylpiperidinium, 1-ethyl-2-methylpiperidinium, mono-, di-, and triethanolammonium, ethylidiethanolammonium, n-butylmonoethanolammonium, tris(hydroxymethyl)methylammonium, phenylmonoethanolammonium, and the like.

It will be apparent to those skilled in the art that the cis-double bond in the synthon (9) may be replaced by a single, triple, or trans-double bond, and that such replacement will not affect the addition of the side chain moiety (8) to the cyclopentanone ring. It is also apparent that the side chain moiety (8) can be resolved before the addition reaction with the synthon (9), or its equivalent, and use of such a resolved intermediate would lead to the optically pure product (13) or (14), as desired.

The following Examples are illustrative of the manner and processes for making the compounds of the invention. All temperatures are in Centigrade.

EXAMPLE 1

1,1-[1,3-Propanediyl-bis(thio)]-n-butan-1-al (2)

A solution of 28.8 g. of 1,3-dithiane in 500 ml. of tetrahydrofuran was treated at −30° to −20° under nitrogen with 150 ml. of 1.6 M n-butyl-lithium and stirred at that temperature for one and a half hours. The mixture was then treated at −30° to −20° with 36.1 g. of 1-bromo-n-butane and stirred at 0° for four hours. The reaction mixture was treated with aqueous ammonium chloride solution and extracted with ether. After washing with brine and drying with magnesium sulfate, the ether solution was evaporated. The residue was distilled at bath temperature 145° under reduced pressure 0.05–0.1 mm Hg to afford 35.0 g. of the title product as an oil, b.p. 70°–72°/0.05 mm Hg. IR: $\lambda_{max}^{film}$ 3.47, 6.9, 7.05, 7.3, 7.9, 8.1, 8.5, 9.1, 10.78, 11.05, 11.57, 13.26 and 13.65μ. NMR: δ4.30 (t, 1,

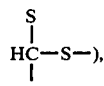

2.94–2.77 (m, 4, —CH$_2$—S$_{13}$), 2.34–1.16 (m, 8, —C—CH$_2$—C—), 0.90 (t, 3, —CH$_2$) ppm.

EXAMPLE 2

3,3-[1,3-Propanediyl-bis(thio)]-n-heptan-2-ol (3)

A solution of 4.8 g. of 1,1-[1,3-propanediyl-bis(thio)]-n-butan-1-al in 40 ml. of dry tetrahydrofuran was treated at −28° to −20° with 17 ml. of 1.6 M n-butyl lithium under nitrogen. After stirring at −30° for two hours, the mixture was treated with 3.12 g. of acetaldehyde. Stirring was continued at −20° to −30° for two hours and then at 0° under a nitrogen blanket overnight. The mixture was diluted with ether, washed, dried and evaporated. Distillation of the crude produce at 0.2 mm Hg pressure afforded 3.5 g. of the title product as an oil, b.p. 115°–118°/0.2 mm Hg. IR: $\lambda_{max}^{film}$ 2.95, 3.44, 6.9, 7.05, 7.25, 7.85, 8.9, 9.2, 9.5, 10.65 and 11.02μ. NMR: δ4.24 (q, 1,

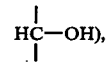

3.26–2.33 (m, 4, —CH$_2$—S—), 2.77 (s, 1, —OH), 1.35 (d,

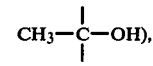

0.90 (t, 3, —CH$_2$—CH$_3$) ppm. Mass spectrum: M+ at m/e 220 (theory 220). Elementary analysis: Calc. C/H/S=54.49/9.14/29.09. Found: C/H/S=54.79/9.28/29.00.

EXAMPLE 3

3,3-[1,3-Propanediyl-bis(thio)]-n-heptan-2-one (4)

An ice-cooled solution of 200 ml. of methylene chloride and 9.6 g. of pyridine was treated at 0° under nitrogen with 6.0 g. of dry chromium trioxide and stirred at 0° for one half hour and at 25° for another half hour. The mixture was then treated at 0° with 2.2 g. of 3,3-[1,3-propanediyl-bis(thio)]-n-heptan-2-ol in 20 ml. of methylene chloride and stirred at room temperature for one hour. The methylene chloride solution was decanted, washed with 5% sodium hydroxide solution, 5% hydrochloric acid solution, sodium bicarbonate solution and brine. After drying and evaporating, the residue was chromatographed on silica gel. Elution with 40% benzene in hexane afforded 1.25 g. of the title product as an oil. IR: $\lambda_{max}^{film}$ 3.42, 5.85, 6.82, 7.03, 7.40, 7.85, 8.50, 9.0, 10.80 and 11.0μ. NMR: δ3.34–2.45 (m, 4, —CH$_2$—S—), 2.35 (s, 3,

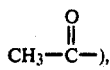

2.20–1.22 (m, 8, C—CH$_2$—C), 0.92 (t, 3, CH$_3$—C) ppm.

EXAMPLE 4

3-Oxo-4,4-[1,3-propanediyl-bis(thio)]-n-octan-1-al (5)

A suspension of 0.48 g. of 50% sodium hydride oil dispersion in 10 ml. of dry benzene was charged at 25° under nitrogen with 0.75 g. of ethylformate in 10 ml. of dry benzene. The mixture was then treated at 25° with three drops of methanol and stirred for five minutes. The solution was treated at 25° with 1.1 g. of 3,3-[1,3-propanediyl-bis(thio)]-n-heptan-2-one in 10 ml. of dry benzene and stirred for three and half hours. The mixture was diluted with brine, acidified with concentrated hydrochloric acid and extracted with ether. The ether extract was washed, dried and evaporated. The residue was chromatographed on silica gel. Elution with benzene afforded 1.15 g. of the title product as a colorless oil. IR: $\lambda_{max}^{film}$ 3.4, 5.8, 5.9, 6.15, 6.32, 7.0, 7.85, 8.0, 8.17, 8.63, 9.3, 10.53, 11.02 and 11.5μ. NMR: δ7.43

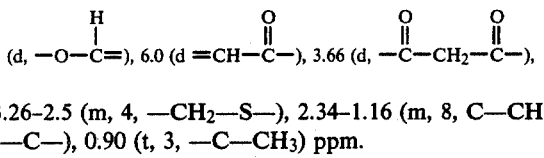

3.26–2.5 (m, 4, —CH$_2$—S—), 2.34–1.16 (m, 8, C—CH$_2$—C—), 0.90 (t, 3, —C—CH$_3$) ppm.

EXAMPLE 5

1-Bromo-4,4-[1,3-propanediyl-bis(thio)]-trans-1-n-hepten-3-one (6)

An ice-cooled solution of 2.2 ml. of 1 M bromine in 2.2 ml. of benzene was treated with 0.57 g. of triphenylphosphine in 20 ml. of benzene and stirred at 25° for ten minutes. The resulting mixture was charged with 0.22 g. of triethylamine in 1 ml. of benzene then treated at 25° with 0.49 g. of 3-oxo-4,4-[1,3-propanediyl-bis(thio)]-n-octan-1-al in 1.4 ml. of benzene. The suspension was stirred at 25° under nitrogen overnight. The mixture was filtered through silica gel and the filtrate was evaporated. The residue was separated by preparative thin layer chromatography using benzene as solvent and afforded 0.35 g. of the title product as an oil. IR: $\lambda_{max}^{film}$ 3.4, 5.9, 6.3, 6.8, 6.9, 7.76, 8.25, 9.3, 10.52 and 10.62μ. NMR: δ7.69 (d, J=14 cps, 1, Br—CH=) 7.34 (d, J=14 cps, 1,

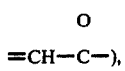

3.34–2.26 (m, 4, —C—CH$_2$—S—), 2.26–1.60 (m, 4, —S—C—CH$_2$—), 1.60–1.10 (m, 4, —C—CH$_2$—CH$_2$—C—), 0.87 (t, 3, —CH$_3$) ppm. Mass spectrum: M$^+$ —C$_4$H$_9$ at m/e 251 (theory 251). UV: $\lambda_{max}^{EtOH}$ 244 mμ (ε8,900).

EXAMPLE 6

1-Bromo-4,4-[1,3-propane-bis(thio)]-trans-1-n-hepten-3-ol (7)

An ice-cooled solution of 1.6 g. of 1-bromo-4,4-[1,3-propanediyl-bis(thio)]-trans-1-n-hepten-3-one in 45 ml. of methanol was treated with 0.19 g. of sodium borohydride and stirred at 0° for one and a half hour. The mixture was diluted with ether, washed, dried, and evaporated. The residue was chromatographed on silica gel. Elution with 30% benzene in hexane afforded 1.05 g. of the title produce as an oil. IR: $\lambda_{max}^{film}$ 2.88, 3.40, 5.82, 6.12, 6.45, 6.80, 7.0, 7.23, 7.80, 8.0, 9.10, 10.63, and 11.0μ.

EXAMPLE 7

1-Bromo-4,4-[1,3-propanediyl-bis(thio)]-3-(trimethylsilyloxy)-trans-1-n-heptene (8)

A solution of 0.93 g. of 1-bromo-4,4-[1,3-propanediyl-bis(thio)]-trans-1-n-hepten-3-ol in 20 ml. of a mixture of ethertetrahydrofuran (3:1), was treated at 25° under nitrogen with 0.14 g. of imidazol. After stirring for 10 minutes, the resulting solution was treated at 25° with 0.25 ml. of trimethylsilyl chloride. Two hours later, the solvent was evaporated and the residue was chromatographed on alumina (grade I). Elution with pentane-ether (10:1) afforded 0.60 g. of the title product as a thin oil. IR: $\lambda_{max}^{film}$ 3.38, 6.15, 7.05, 7.98, 9.16, 10.63, 11.4, 11.85, and 13.3μ. NMR: δ6.56 (d,d, J=14, 7 cps, —C=CH—C—O—), 6.30 (d, J=14 cps, Br—CH=), 4.4 (d, J=14 cps, HC—O—), 3.2–2.2 (m, 4, —CH$_2$—S—), 2.10–1.16 (m, 8, —C—CH$_2$—C—), 0.92, (t, 3, CH$_3$—C—) ppm. Mass spectrum: M$^+$ —CH$_3$ at m/e 367 (theory 367).

EXAMPLE 8

(5Z, 11α, 13E, 15RS)-9-oxo-16,16-[1,3-propanediyl-bis(thio)]-11-(tetrahydropyran-2-yl)oxy-15-(trimethylsilyloxy)-prosta-5,13-dien-1-oic acid, methyl ester (10)

A solution of 1.91 g. of 1-bromo-4,4-[1,3-propanediyl-bis(thio)]-3-(trimethylsilyloxy)-trans-1-n-heptene in 20 ml. of ether under nitrogen was cooled in a dry-ice acetone bath and treated with 8.34 ml. of 1.24 M t-butyl lithium in pentane. After stirring at −78° for two hours, a freshly prepared solution of 1.63 g. of hexamethylphosphorous-triamide and 0.65 g. of n-proplyethynyl copper in 10 ml. of ether was added to the reaction mixture and stirring continued for one hour under nitrogen at −78°. A solution of 0.805 g. of 7-(5-oxo-1-cyclopentenyl)-cis-5-heptenoic acid, methyl ester in 10 ml. of ether was then added and the mixture stirred at −78° for one hour, at −30° for two hours and at 0° for an additional half hour. The reaction mixture was poured into a saturated ammonium sulfate solution, extracted with ether and the extract washed with ice cold 10% sulfuric acid, filtered through Celite, washed with bicarbonate solution, brine, and dried. After evaporation of the solvent, the residue was chromatographed on silica gel. Elution with 7.5% ethyl acetate in hexane afforded 0.80 g. of the title product as an oil. IR: $\lambda_{max}^{film}$ 3.46, 5.78, 7.0, 7.46, 8.04, 8.70, 8.90, 9.30, 9.67, 10.30, 11.0, 11.35, 11.90, and 13.32μ. NMR: δ5.80 (m, 2, 13 and 14-H), 5.40 (m, 2, 5 and 6-H), 4.68 (m, 1,

4.40 (d, 1, 15-H), 4.04 and 3.33 (m, 3, —CH$_2$—O and 11-H), 0.90 (t, 3, 20-CH$_3$), 0.15 (s, 9, Si-CH$_3$) ppm. Mass spectrum: MH$^+$-TMSOH at m/e 537 (theory 537), MH$^+$-THP at m/e 453 (theory 453), MH$^+$-THP-TMSOH at m/e 435 (theory 435).

EXAMPLE 9

(5Z,11α,13E,15S)-11,15-Dihydroxy-9-oxo-16,16-[1,3-propanediyl-bis(thio)]-prosta-5,13-dien-1-oic acid, methyl ester (12)

and (5Z,11α,13E,15R)-11,15-Dihydroxy-9-oxo-16,16-[1,3-propanediyl-bis(thio)]-prosta-5,13-dien-1-oic acid, methyl ester (11)

A solution of 0.70 g. of (5Z,11α,13E,15RS)-9-oxo-16,16-[1,3-propanediyl-bis(thio)]-11-(tetrahydro-pyran-2-yl)oxy-15-(trimethylsilyloxy)-prosta-5,13-dien-1-oic acid, methyl ester in 5 ml. of glacial acetic acid and 2.5 ml. of water was stirred at 40°for three hours under nitrogen. The reaction mixture was evaporated and the residue chromatographed on silica gel. Elution with 35% ethyl acetate in hexanes afforded 0.11 g. of the first title produce as an oil. IR: $\lambda_{max}^{film}$ 2.85, 3.38, 5.70, 6.92, 8.03, 9.25, 10.28, 10.95, and 11.50μ. NMR: δ5.88 (m, 2, 13 and 14-H), 5.40 (m, 2, 5 and 5-H), 4.57 (d, 1, 15-H), 4.09 (q, 1, 11-H), 3.67 (s, 3, —O—CH$_3$), 3.08 (s, 2, —OH), 0.91 (t, 3, —C—CH$_3$) ppm. Mass spectrum: MH$^+$—H$_2$O at m/e 453 (theory 453).

Continuing elution with 35% ethyl acetate in hexanes afforded 0.07 g. of the second title product as an oil. IR: 2.90, 3.40, 5.72, 6.95, 7.35, 8.0, 8.60, 9.25, 9.70, 10.28 and 11.0μ. NMR: δ5.85 (m, 2, 13 and 14-H), 5.39 (m, 2, 5 and 6-H), 4.52 (d, 1, 15-H), 4.08 (q, 1, 11-H), 3.67 (s, 3, —O—CH$_3$), 2.20 (s, 2, OH), 0.91 (t, 3, —C—CH$_3$) ppm. Mass spectrum: MH$^+$—H$_2$O at m/e 453 (theory 453).

EXAMPLE 10

(5Z,13E,11α,15S)-11,15-Dihydroxy-9,16-dioxo-prosta-5,13-dien-1-oic acid, methyl ester (14) [16-Keto prostaglandin E$_2$ methyl ester]

and (5Z,13E,11α,15R)-11,15-Dihydroxy-9,16-dioxo-prosta-5,13-dien-1-oic acid, methyl ester (13) [15-epi-16-keto prostaglandin E$_2$ methyl ester]

A stirring solution of 1.52 g. of silver nitrate and 1.07 g. of chlorosuccinimide in 25 ml. of 80% aqueous acetonitrile solution was treated with 1.25 g. of (5Z,11α,1-3E,15RS)-9-oxo-16, 16-[1,3-propanediyl-bis(thio)]-11-(tetrahydro-pyran-2-yl)-oxy-15-(trimethylsilyloxy)pros-ta-5,13-dien-1-oic acid, methyl ester in 25 ml. of 80% aqueous acetonitrile. The reaction mixture was stirred at 25° for one hour under nitrogen, and was then treated with 2 ml. of sodium sulfite solution, 2 ml. of sodium carbonate solution, 2 ml. of brine and 200 ml. of methylene chloride-hexanes (1:1) mixture. The whole mixture was filtered through Celite, washed with brine and dried. After evaporation of the solvent, the residue was treated with a mixture of acetic acid-water-tetrahydrofuran (4 ml.-2 ml.-2 ml.) and stirred at 25° for one and a half hours under nitrogen. The reaction mixture was evaporated and the residue chromatographed on silica gel. Elution with 50% ethyl acetate in hexanes afforded 0.07 g. of the first title product (14) as an oil. IR: $\lambda_{max}^{film}$ 2.90, 3.39, 5.80, 5.87 (shoulder), 6.93, 7.30, 8.02, 8.60, 9.23, 9.70 and 10.23μ. NMR: δ5.80 (m, 2, 13 and 14-H), 5.35 (m, 2, 5 and 6-H), 4.62 (d, 1, 15-H), 4.12 (q, 1, 11-H), 3.90 (m, 2, OH), 3.68 (s, 3, —O—CH$_3$), 0.90 (t, 3, —C—CH$_3$) ppm. Mass spectrum: MH$^+$—H$_2$O at m/e 363 (theory 363).

Continuing elution with 50% ethyl acetate in hexanes afforded 0.09 g. of the second title product (13) as an oil. IR: $\lambda_{max}^{film}$ 2.90, 3.38, 5.68, 5.86, 6.90, 7.30, 7.56, 8.0, 8.59, 9.0, 9.25, 9.64, and 10.20μ. NMR: δ5.75 (m, 2, 13 and 14-H), 5.39 (m, 2, 5 and 6-H), 4.59 (d, 1, 15-H), 4.10 (q, 1, 11-H), 4.00 (m, 2, OH), 3.66 (s, 3, —O—CH$_3$), 0.90 (t, 3, —C—CH$_3$) ppm. Mass spectrum: MH$^+$ at m/e 381 (theory 381).

What is claimed is:

1. A compound of the formula:

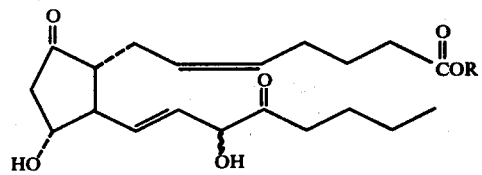

wherein R is hydrogen, an alkyl group of from 1 to 6 carbon atoms, an alkali metal, or a pharmaceutically acceptable non-toxic cation derived from ammonia or a basic amine.

2. The compound of Formula I which is (5Z,13E,1-1α,15S)-11,15-dihydroxy-9,16-dioxo-prosta-5,13-dien-1-oic acid, methyl ester.

3. The compound of Formula I which is (5Z,13E,1-1α,15R)-11,15-dihydroxy-9,16-dioxo-prosta-5,13-dien-1-oic acid, methyl ester.

* * * * *